June 26, 1973 W. E. DUFFETT Plant Pat. 3,369
CHRYSANTHEMUM PLANT
Filed Aug. 13, 1971
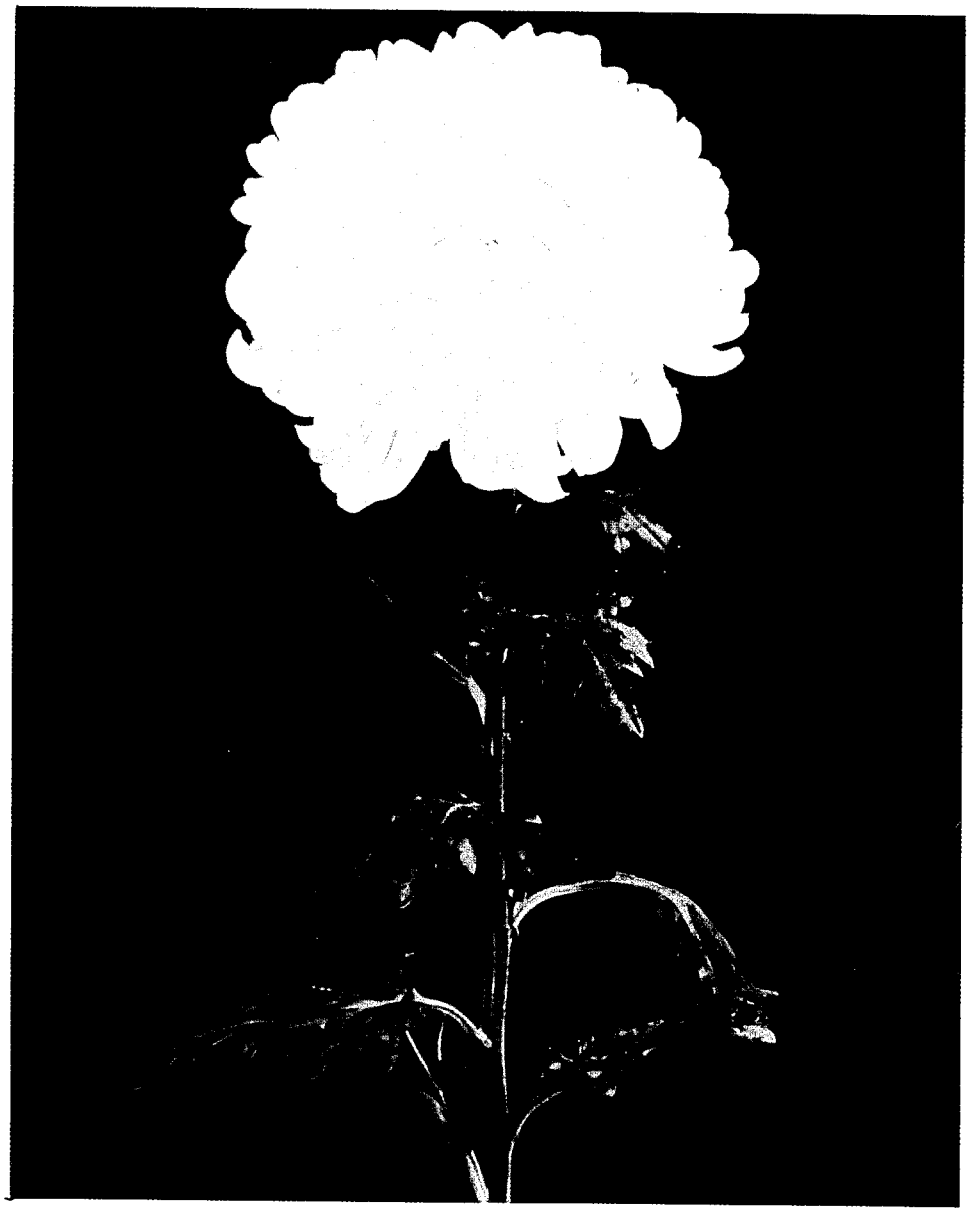

United States Patent Office

Plant Pat. 3,369
Patented June 26, 1973

3,369

CHRYSANTHEMUM PLANT

William E. Duffett, Akron, Ohio, assignor to Framptons Nurseries Limited, Sussex, England

Filed Aug. 13, 1971, Ser. No. 171,781
Int. Cl. A01h *5/00*
U.S. Cl. Plt.—78 1 Claim

This invention relates to a new and distinct variety of *Chrysanthemum morifolium* Bailey (Standard type) hereinafter referred to as Yellow Snowdon. Yellow Snowdon is a yellow sport from the variety Snowdon found in May 1969 by me in cultivated ground at Barberton, Ohio. The variety Snowdon was originated by Barrie John Machin from a cross made in England between a seedling 33D4 (which originated from a cross between the varieties Explorer and Jonquil) and the variety Colombia, the former being the seed parent and the latter being the pollen parent.

The variety Snowdon resulted from an extensive breeding program with the object of producing improved year ground standards for year round chrysanthemum production programs with improved uniformity and response over existing varieties, with particular emphasis on winter production. Snowdon fulfills the need for a new white standard. The yellow sport hereinafter referred to as Yellow Snowdon is distinguished from Snowdon by its clearly yellow color.

The following unique combination of characteristics distinguish Yellow Snowdon from Sunburst Mefo, the most similar yellow year around standard grown in Great Britain of which I am aware:

(1) It is more responsive all year round, especially under poor light and marginal temperature conditions. Flowering time in short days can be reduced by one week or ten days compared with Sunburst Mefo according to season.

Although both Yellow Snowdon and Sunburst Mefo are lised as varieties of 10 week response this is a convenient average measure to use. In fact, Yellow Snowdon tends to flower in 9 weeks in summer and 10 weeks in winter. Sunburst Mefo takes 10 weeks in summer and up to 11½ weeks in winter in Europe.

This is why, although both are listed as 10 week varieties, the response of Yellow Snowdon can be one week or ten days in advance of Sunburst Mefo in winter conditions.

(2) Production is much more uniform and a higher percentage grade of market flowers is obtained.

(3) There are no problems with damping off of flowers under humid conditions.

(4) Although flower size is slightly smaller with Yellow Snowdon, the depth of flower is greater and therefore a more incurved shape of bloom is produced. Yellow Snowdon has more disc petals than Sunburst Mefo, but even when the bloom is fully mature these are covered by the incurving inner ray petals.

Asexual reproduction of this new variety as performed at Yoder Brothers, Inc., in Barberton, Ohio, by rooting vegetative shoots, shows that the above characteristics are fixed and come true to type and are transmitted through succeeding generations.

The accompanying drawing shows a typical flower of new variety depicted in color as nearly true as it is reasonably possible to make same in a color illustration of this character.

The following is a detailed description of the new variety Yellow Snowdon with color terminology in accordance with the Royal Horticultural Society Color Chart (RHS).

Genus: Chrysanthemum.
Species: *Morifolium* Bailey.
Type: Standard.
Class: Incurving decorative.
Breeding: Sport from Snowdon found at Yoder Bros. Inc., Barberton, Ohio, U.S.A. in May 1969. Snowdon is a cross between a year around seedling 33D4 and Colombia, the former being the seed parent and the latter being the pollen parent, and was developed at Framptons Nurseries Ltd., Forbridge Nursery, Chichester, Sussex, England. Seedling 33D4 was a cross between the varieties Explorer and Jonquil.
Propagation: Holds its distinguishing characteristics through succeeding propagations by rooting vegetative shoots.
Bloom size: Average diameter 13 cms. Average depth 11 cms. when fully open.
Petalage: 220 to 250 ray petals, 30 to 100 disc petals.
Form: Incurving decorative.
Petals: Broad, overlapping, blunt, boat-shaped with medium texture.
Color of open bloom: Inner face of fully expanded petal RHS 6B. Outer face of fully expanded petal RHS 7D. Inner face of young petal RHS 6B, outer face of young petal RHS 7D.
Response Group: 10 weeks.
Temperature tolerance: 55–60° F. at night.
Plant: Wiry upright habit of growth.
Foliage: Good quality. Average internode length 2½ to 3 cm. Small size-color RHS 137A-medium texture.
Stem: Medium thickness and wiry.
Colour of stem at flowering: RHS 146 C.

I claim:

1. A new and distinct variety of *Chrysanthemum morifolium* Bailey, substantially as herein shown and described, characterized particularly as to novelty by the unique combination of a wiry, upright plant with incurving, decorative yellow flowers having from 220 to 250 ray petals and 30 to 100 disc petals, excellent resistance to damping off under humid conditions, and an improved response time of 1½ weeks during short day seasons in poor light conditions.

No references cited.

ROBERT E. BAGWILL, Primary Examiner

UNITED STATES PATENT OFFICE

CERTIFICATE OF CORRECTION

Patent No. Plant 3369 Dated June 26, 1973

Inventor(s) WILLIAM E. DUFFETT

It is certified that error appears in the above-identified patent and that said Letters Patent are hereby corrected as shown below:

Claims Priority of British Application No. AFP 1524, filed March 29, 1971

Signed and sealed this 1st day of January 1974.

(SEAL)
Attest:

EDWARD M.FLETCHER,JR.
Attesting Officer

RENE D. TEGTMEYER
Acting Commissioner of Patents

USCOMM-DC 60376-P69
☆ U.S. GOVERNMENT PRINTING OFFICE : 1969 O—366-334.